(12) United States Patent
Beall

(10) Patent No.: US 8,501,147 B2
(45) Date of Patent: Aug. 6, 2013

(54) METHOD AND SYSTEM FOR PRODUCING GRAPHENE AND GRAPHENOL

(71) Applicant: Gary Beall, San Marcos, TX (US)

(72) Inventor: Gary Beall, San Marcos, TX (US)

(73) Assignee: National Nanomaterials, Inc., Austin, TX (US)

( * ) Notice: Subject to any disclaimer, the term of this patent is extended or adjusted under 35 U.S.C. 154(b) by 0 days.

(21) Appl. No.: 13/659,570

(22) Filed: Oct. 24, 2012

(65) Prior Publication Data

US 2013/0112925 A1  May 9, 2013

Related U.S. Application Data

(63) Continuation of application No. 13/004,732, filed on Jan. 11, 2011, now Pat. No. 8,361,430.

(60) Provisional application No. 61/335,707, filed on Jan. 12, 2010.

(51) Int. Cl.
*C01B 31/04* (2006.01)

(52) U.S. Cl.
USPC .......................................... 423/448; 423/460

(58) Field of Classification Search
USPC ................................. 423/448, 460
See application file for complete search history.

(56) References Cited

FOREIGN PATENT DOCUMENTS

WO    WO 2009065018 A1 *  5/2009

OTHER PUBLICATIONS

Functionalized Single Graphene Sheets Derived from Splitting Graphite Oxide Hannes C. Schniepp, Je-Luen Li,±, Michael J. McAllister, Hiroaki Sai, Margarita Herrera-Alonso, Douglas H. Adamson, Robert K. Prud'homme, Roberto Car, Dudley A. Saville and Ilhan A. Aksay The Journal of Physical Chemistry B 2006 110 (17), 8535-8539.*

Evolution of Carbon Microstructures during the Pyrolysis of Turkish Elbistan Lignite in the Temperature Range 700-1000° C Billur Sakintuna and, Yuda Yürüm, and Sevil çetinkaya Energy & Fuels 2004 18 (3), 883-888.*

* cited by examiner

*Primary Examiner* — Daniel C McCracken
*Assistant Examiner* — Richard M Rump
(74) *Attorney, Agent, or Firm* — Hulsey, P.C.; Loren T. Smith; William N. Hulsey, III

(57) ABSTRACT

This disclosure includes a process that unexpectedly can produce very inexpensive graphene and a new compound called graphenol in particulate or dispersions in solvents. The process can also produce graphene layers on metallic and nonmetallic substrates. Further, the graphenol and graphene can be utilized to form nanocomposites that yield property improvements exceeding anything reported previously.

7 Claims, 9 Drawing Sheets

METHOD AND SYSTEM FOR PRODUCING GRAPHENE AND GRAPHENOL

CROSS-REFERENCE TO RELATED APPLICATIONS

This application is a continuation of U.S. patent application Ser. No. 13/004,732 filed Jan. 11, 2011, which claims priority to U.S. Provisional Patent Application Ser. No. 61/335,707 filed Jan. 12, 2010. Each is hereby incorporated by reference in its entirety for all purposes.

FIELD

This disclosure relates generally to the field of graphene and nanocomposites. Specifically, this disclosure relates to new, cost-effective methods of producing graphene and related materials.

BACKGROUND

The discovery of graphene in 2004 has sparked enormous scientific interest. This interest is largely due to the very interesting properties of graphene, which include an extremely large surface area (~2630 $m^2g^{-1}$), high intrinsic mobility (~200,000 $cm^2 V^{-1} s^{-1}$), high Young's modulus (~1 TPa), thermal conductivity (~5,000 $\mu m^{-1} K^{-1}$), and optical transmittance (~97.7%).

This suite of properties is superior to those observed for carbon nanotubes. In the case of carbon nanotubes, similar interest was generated when they were first discovered. The dream of new materials from carbon nanotubes has largely been unfulfilled due to the high cost of producing the carbon nanotubes. This same high cost situation currently exists with graphene. The original discovery of graphene utilized the sticky tape method. This method obviously can only be used for research purposes. A second method involves the epitaxial growth of SiC followed by thermal treatment to produce a layer of graphene. Chemical vapor deposition has also been shown to grow graphene on copper substrates. A wet chemical method of producing graphene involves the strong oxidation of graphite to produce graphene oxide followed by strong chemical reduction. The most promising known process is the graphene oxide; however, it begins with an expensive starting material. Another route to nanostructured materials and graphene is a method involving pyrolysis of polymers. In a slightly different approach to the exfoliation of graphite, supercritical fluids are utilized to accomplish exfoliation. A method for producing dispersions of graphite, graphite oxide and some graphene has been reported by utilizing ultrasound and surfactants. All of these processes are expensive and difficult to scale up to industrial scale.

Two of the critical properties of graphene are its strength and high surface area. If graphene can be fully exfoliated in polymers, the resulting nanocomposite may exhibit extraordinary strength. It may also potentially impart high electrical and thermal conductivity. There have been a number of patents reportedly utilizing graphene to make such nanocomposites. These composites, however, have not produced extraordinary property improvements.

SUMMARY

Therefore, it is an object of this disclosure to provide a new method of producing graphene and related nanocomposites having desired material properties.

This disclosure includes a process that unexpectedly can produce very inexpensive graphene and a new compound called graphenol in particulate or dispersions in solvents. The process can also produce graphene layers on metallic and nonmetallic substrates. Further, the graphenol and graphene can be utilized to form nanocomposites that yield mechanical property improvements exceeding anything reported previously.

These and other advantages of the disclosed subject matter, as well as additional novel features, will be apparent from the description provided herein. The intent of this summary is not to be a comprehensive description of the subject matter, but rather to provide a short overview of some of the subject matter's functionality. Other systems, methods, features and advantages here provided will become apparent to one with skill in the art upon examination of the following FIGURES and detailed description. It is intended that all such additional systems, methods, features and advantages included within this description, be within the scope of the claims.

BRIEF DESCRIPTION OF THE DRAWINGS

The features, nature, and advantages of the disclosed subject matter will become more apparent from the detailed description set forth below when taken in conjunction with the accompanying drawings, wherein.

DETAILED DESCRIPTION

Although described with reference to specific embodiments, one skilled in the art could apply the principles discussed herein to other areas and/or embodiments.

Those with skill in the art will recognize that the disclosed embodiments have relevance to a wide variety of areas in addition to those specific examples described below.

It has been discovered unexpectedly that graphene and a new compound, called graphenol, can be made from naturally occurring extracts from natural materials such as lignite, leonardite, peats, etc. (referred to generally as carbonaceous materials). The following is an overview of the disclosed process for producing graphenol and graphene:

First, the humic acid portion of a carbonaceous material is extracted with a strong base The solution is filtered and then reduced chemically with hydrazine or elemental hydrogen The graphenol solution is then passed through an ion exchange resin to remove the cations of the base (or if ammonium hydroxide is used as the base, heating may be used to expel ammonia and water)

In the final step, the graphenol may be converted to graphene by pyrolysis under argon and/or an argon/hydrogen mixture at above approximately 400° C.

The disclosed process for producing graphenol and graphene starts with leonardite, lignite, peat, or another suitable carbonaceous material as a naturally occurring source of humic acid. Leonardite is a highly oxidized lignite coal that occurs in large deposits in North Dakota and many other geographical locations around the world. Leonardite is normally associated with lignite deposits and is thought to be highly oxidized lignite. This leonardite typically contains a humic-acid-like material that constitutes approximately 75-85% of its mass. Lignite and peat generally contain smaller amounts of humic acid.

Figure 1:
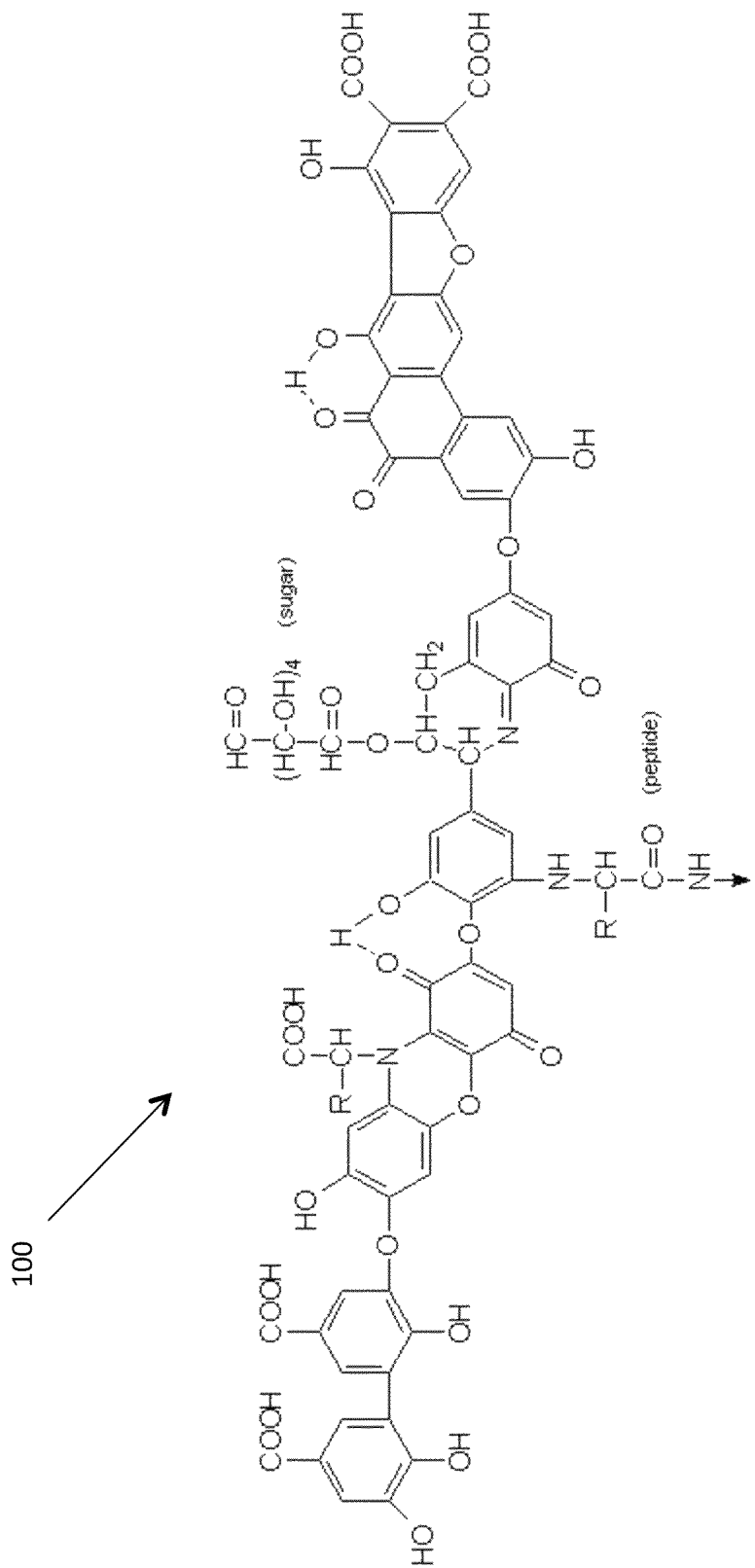
FIG. 1 shows an idealized structure of humic acid from soil.

Humic acid is a soil term that is the organic portion contained in soil that is extractable in strong base and precipitates in acid solution. "Humic acid" does not refer to a single compound; the structure is very dependent on the source. Soil scientists have proposed a generalized structure that focuses mainly on the identifiable functionalities that render humic acid soluble in base. This is illustrated as structure 100 in FIG. 1. Generally, the humic acid in soil is of low molecular weight and if reduced would only yield molecules of very small lateral dimensions.

The humic acid in leonardite is different from soil humic acid in that it has many more fused rings in the interior, and the molecular weight is much higher. Surprisingly, the molecular weights appear to be so large that the base extracted material is actually a colloidal suspension. Conventional molecular weight determinations have not recognized this and therefore would have drawn the conclusion that reduction of these base extracts would only yield low molecular weight compounds.

This material is extracted utilizing a strong base. The most common bases used in this step are sodium, potassium or ammonium hydroxides. Any strong base may be used, but the critical factor is that the carboxylic acid functionality must be converted to a carboxylate ion, which results in the formation of stable suspensions.

The next step is to chemically reduce the carboxylic acids of the dissolved humic acid. This step has been accomplished in two ways.

Figure 2B:
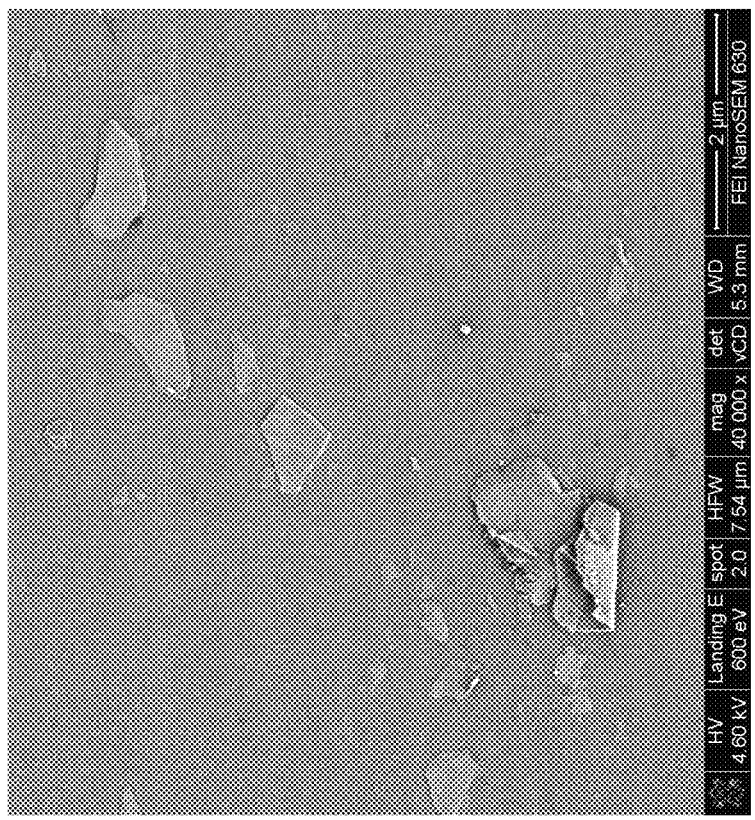
FIGS. 2A and 2B show scanning electron micrographs of graphenol produced in accordance with the present disclosure.
Figure 2A:
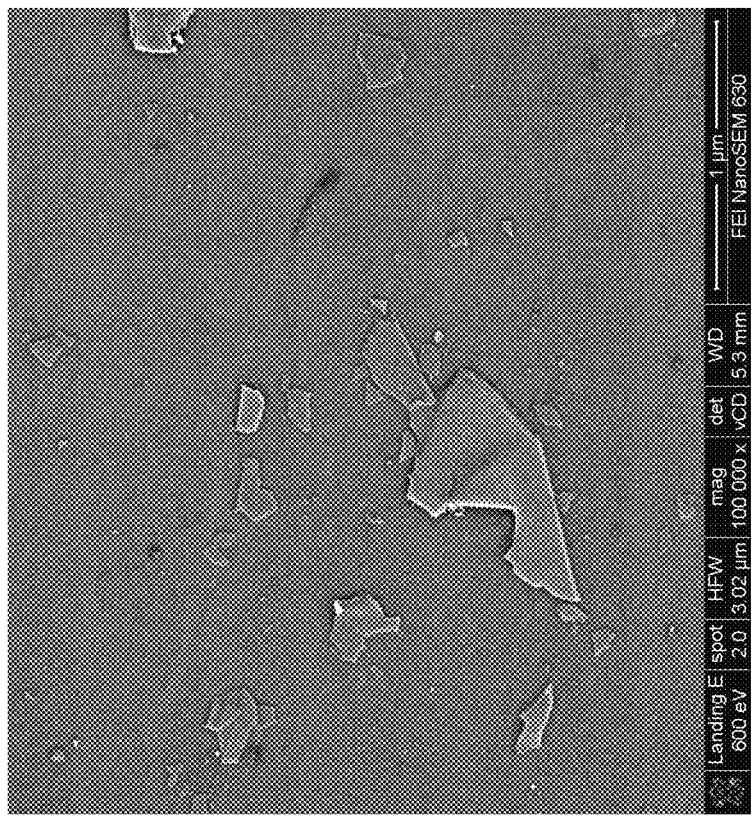

The first method is accomplished by placing the solution of humic acid in a pressure reactor with a hydrogenation catalyst or catalysts and then purging the vessel with argon followed by hydrogen. The vessel thus charged with the humic acid solution, catalysts, and hydrogen is then heated and stirred to effect the reduction of the carboxylic groups into alcoholic groups on the humic acid. The solution is then filtered or centrifuged to remove the catalysts. The degree of reduction may be tested at this point by acidifying the solution. If the humic acid has residual carboxylic acid groups, it will precipitate as the pH is lowered below approximately 2-3. At this stage, the nanoparticles are what we call "graphenol," which is believed to be a novel compound. These colloidal suspensions are very stable and have remained suspended for months in the laboratory. Samples of solution from this step were spin coated onto mica and imaged with a scanning electron microscope, as shown in FIGS. 2A and 2B. The size of the graphenol flakes was quite surprising and was completely unexpected. This can be illustrated by calculating the molecular weight of a graphene particle that is one atom thick and 0.5 microns in the other two dimensions. The molecular weight would be ~170,000,000, which is much larger than any molecular weights reported for humic acids.

The second method utilizes hydrazine as the reductant. In this method the humic acid is either extracted using a strong base solution or dimethylformamide and then treated with hydrazine. The characterization of this material again indicates that it is graphenol. This method may be less advantageous industrially due to the toxicity of hydrazine, but it illustrates the fact that the reduction step can be carried out utilizing a number of reducing agents.

Figure 7:
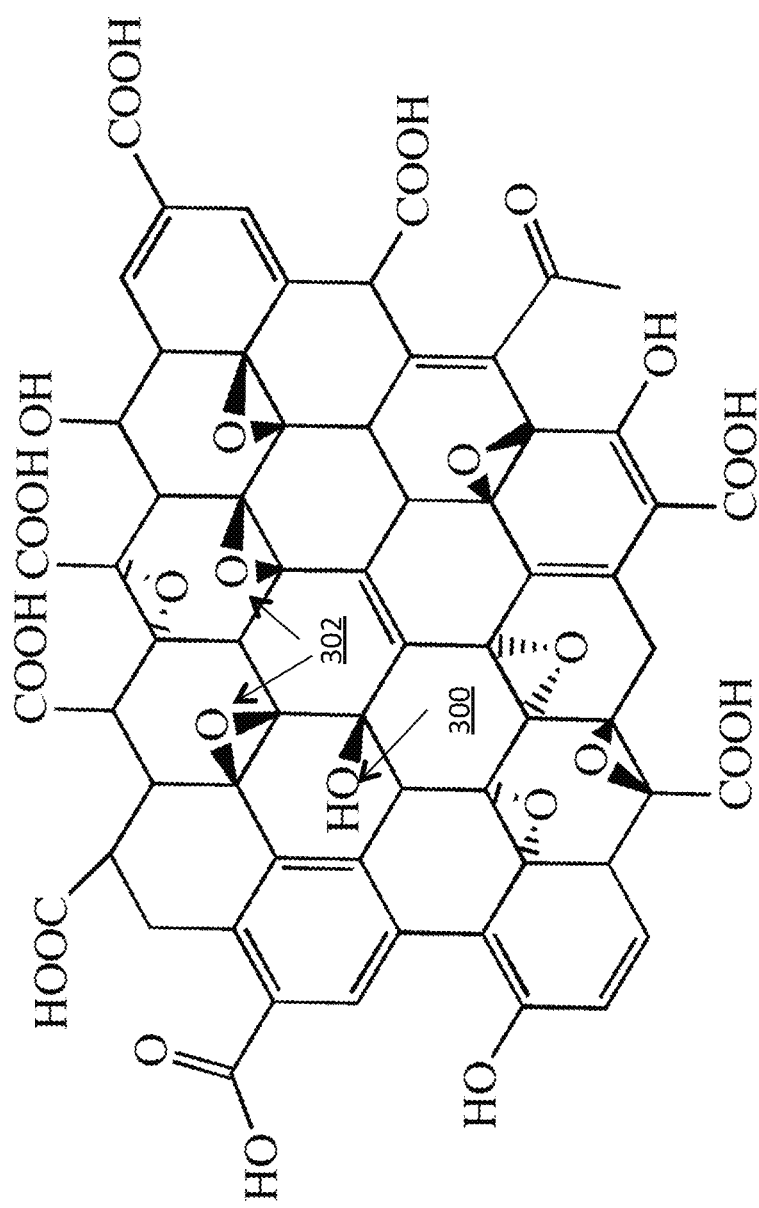
FIG. 7 shows an idealized structure of graphene oxide.

FIG. 7 shows an idealized structure of graphene oxide (GO). As can be seen, the conjugated structure of double bonds has been destroyed by phenolic groups 300 and epoxide groups 302. The result of this is that graphene oxide dispersions exhibit a light amber color. When GO is chemically reduced the suspensions become quite black because much of the conjugated aromatic structure is restored. It is clear however that the structure retains some defects since electrical conductivity is never recovered completely.

Figure 8:
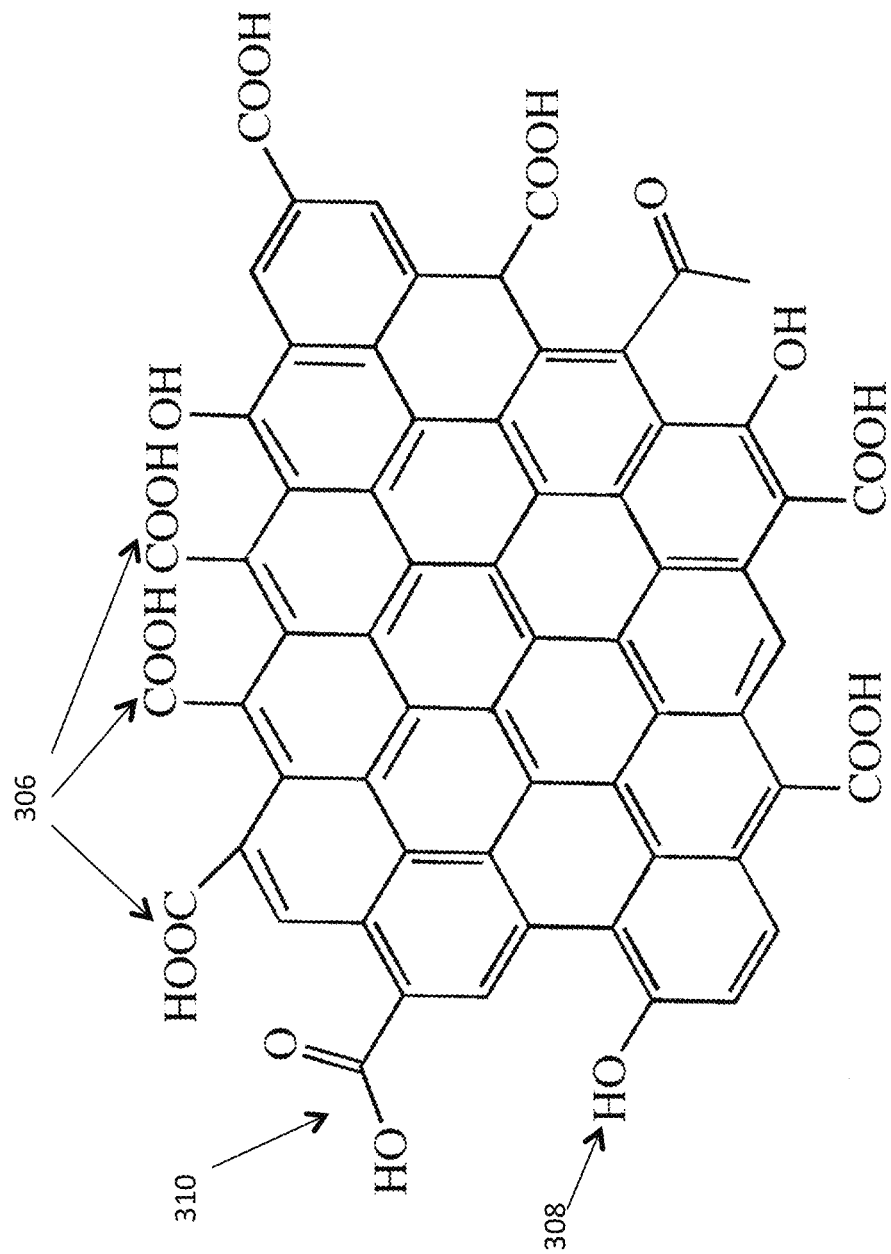
FIG. 8 shows an idealized structure of humic acid extracted from leonardite, lignite, or peat.

FIG. 8 shows an idealized structure of humic acid extracted from leonardite, lignite, peat, or another suitable carbonaceous material. The structure of this humic acid appears to be different from GO. As shown, the conjugate aromatic core is intact, and the edges are studded with carboxylic acid groups 306, phenol groups 308 and aldehyde of ketone groups 310. This structure is consistent with the very black color of base extracted solutions of humic acid derived from leonardite. It is quite different from humic acid derived from soil. The reduction of the structure in FIG. 8 results in the new compound that we call graphenol.

Figure 9:
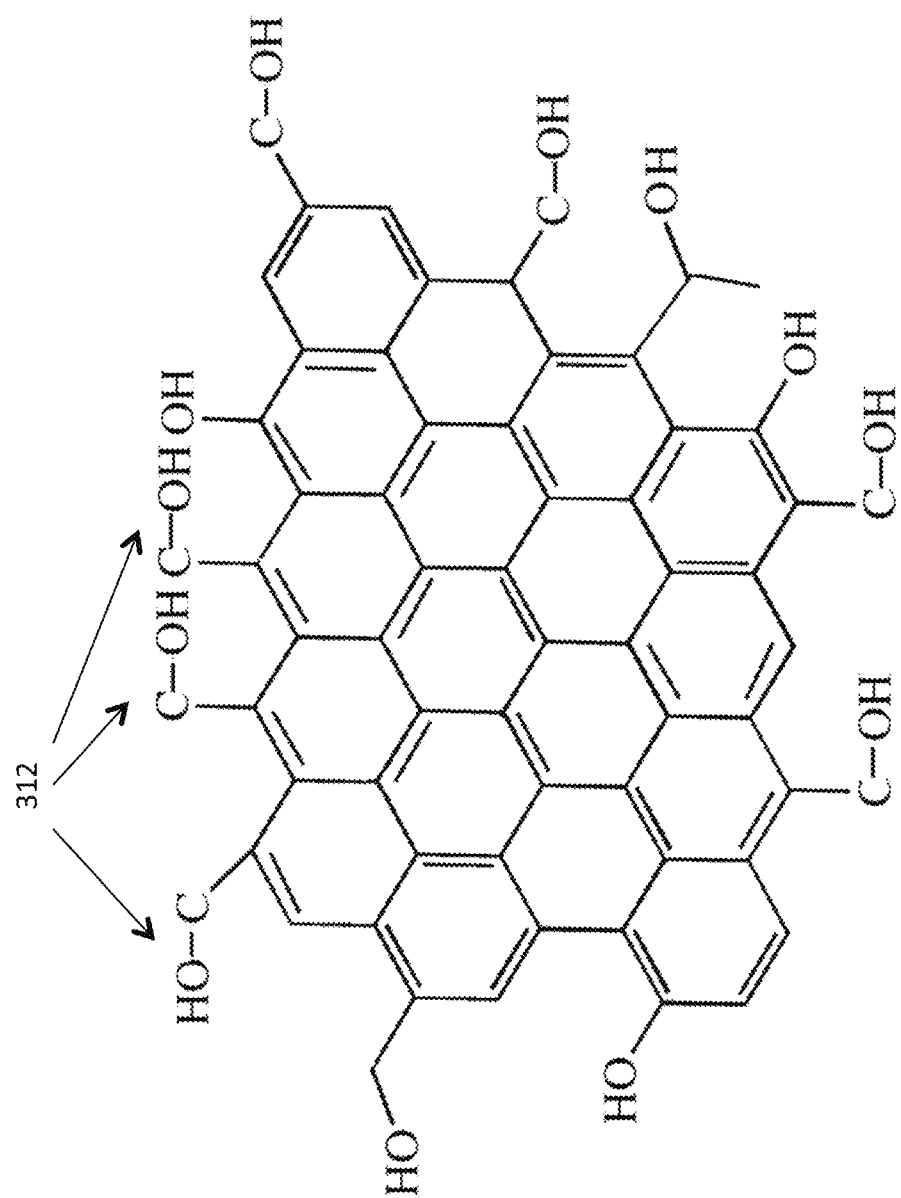
FIG. 9 shows an idealized structure of graphenol.

FIG. 9 shows the idealized graphenol structure and illustrates that the carboxylic groups 306 have been converted to alcohol groups 312. The core is unchanged and affords the ability to conduct chemistry only at the edges which could yield strong interactions in composites.

Figure 6:
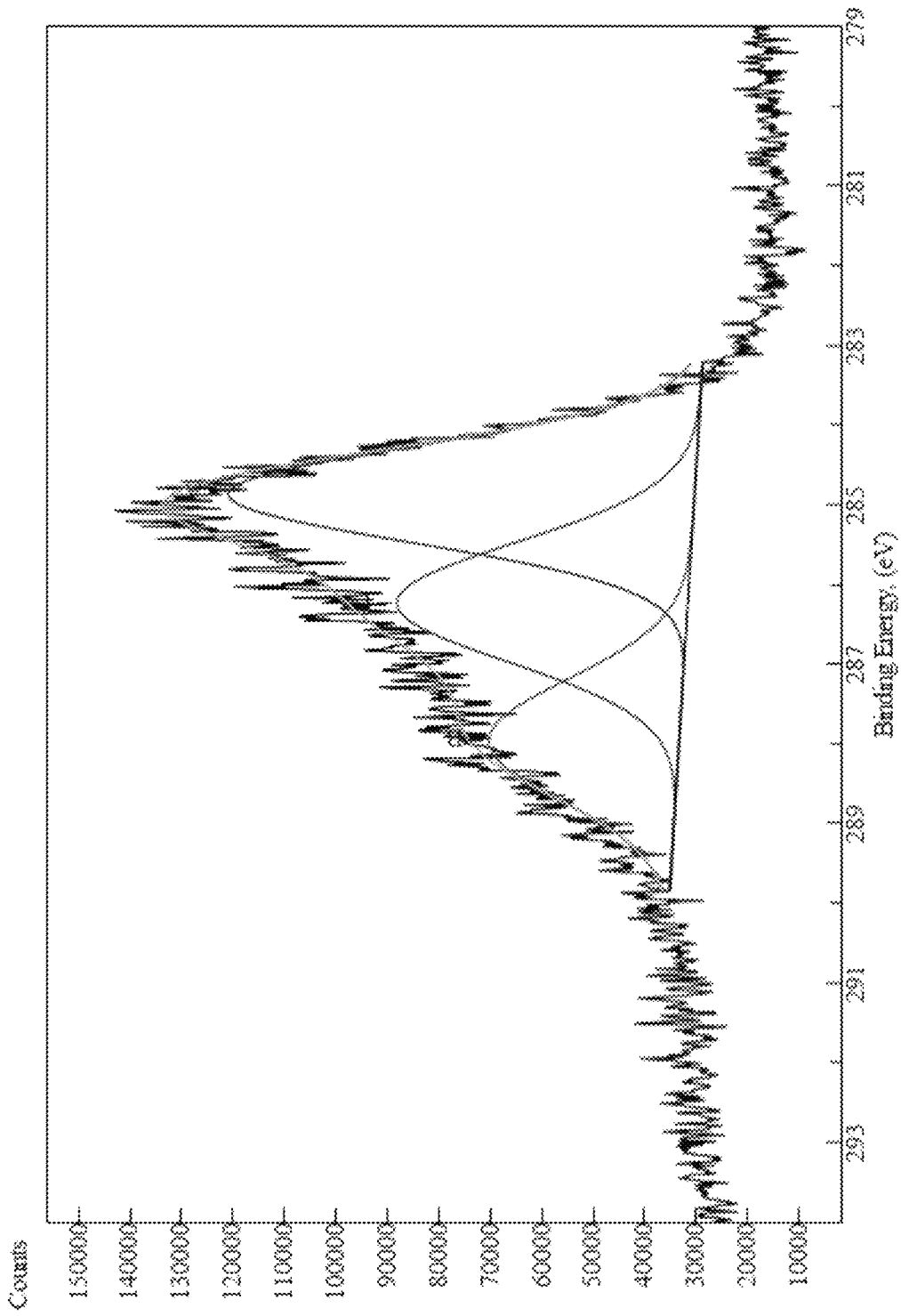
FIG. 6 shows a screenshot of an X-ray photoelectron spectrum analysis of humic acid after reduction with hydrazine and pyrolysis.

The dispersion of graphenol from either process is then passed through a strong acid ion exchange resin in the acid form to remove the cations from the base utilized to dissolve the carbonaceous material. Alternatively, if ammonium hydroxide is used, the ammonia may be driven off by heating. In order to produce graphene, the ion exchanged solution of graphenol is dried and then placed in a furnace under an atmosphere of argon, typically at between approximately 400 to 800° C. The product from this step appears to be graphene, as can be seen in FIG. 6. In this step the reduction can be accelerated by including a small partial pressure of hydrogen in the argon. The main methods of identifying the graphene include X-ray diffraction, SEM, AFM, and four point probe resistance measurements. At this step, the typical X-ray diffraction peak appears for graphite and becomes stronger the higher the temperature and the length of pyrolysis.

Figure 3:
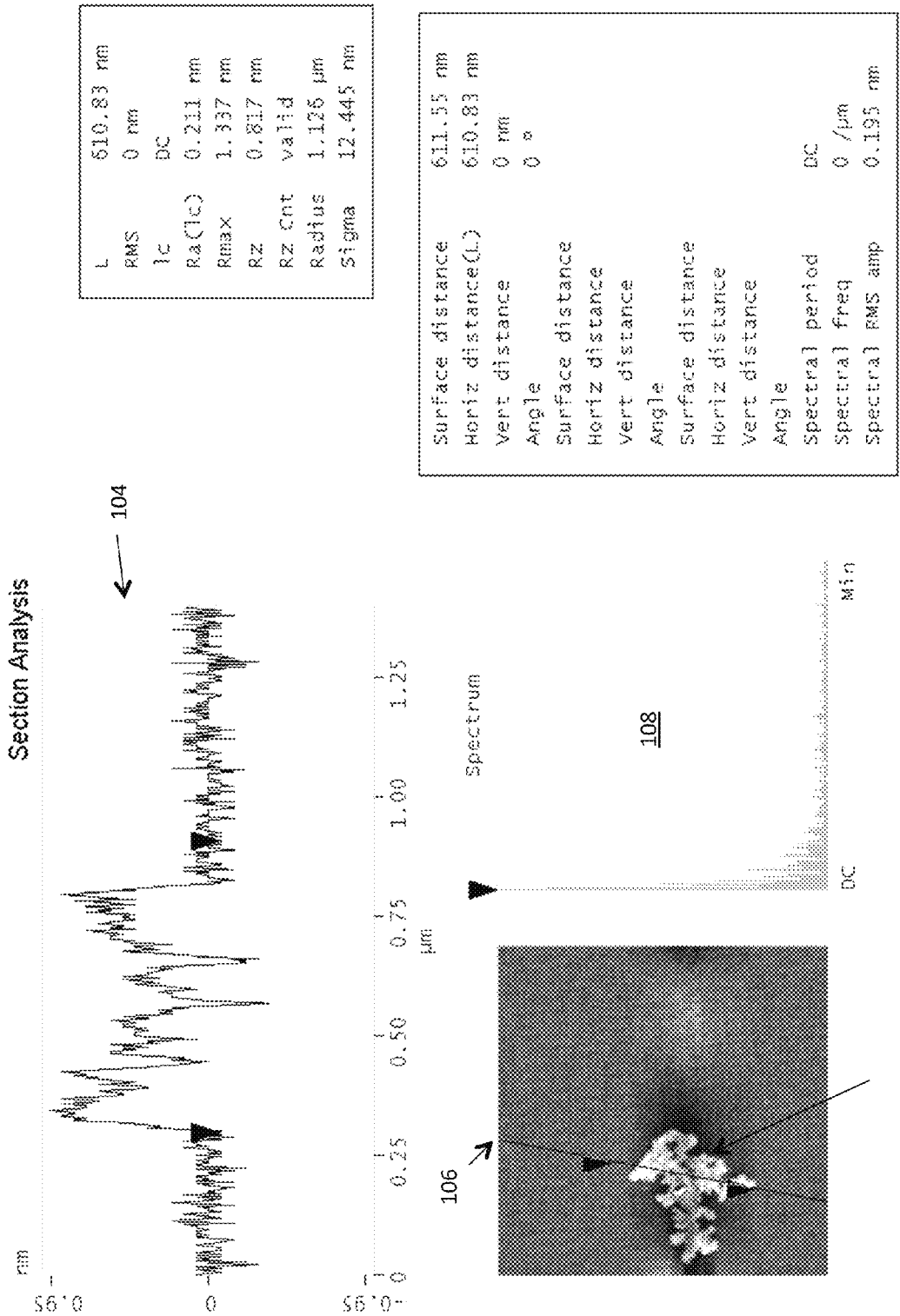
FIG. 3 shows a screenshot of an atomic force microscopy analysis of a graphenol particle.

Further analysis of these flakes with atomic force microscopy (AFM) as shown in FIG. 3 demonstrates that the thickness of these particles is in the range of approximately 0.3 to 0.7 nanometers. The thickness of graphenol flake 102 is shown in AFM graph 104 along axis 106. The Fourier transform of graph 104 is shown in spectrum 108. One sheet of graphene is nominally 0.34 nanometers. Based on X-ray photoelectron spectroscopy (XPS) and infrared spectroscopy (IR), this material is a new compound we call graphenol. In graphenol, the carboxylic groups have been reduced to alcohol groups and any phenolic groups originally present still exist.

Figure 4:
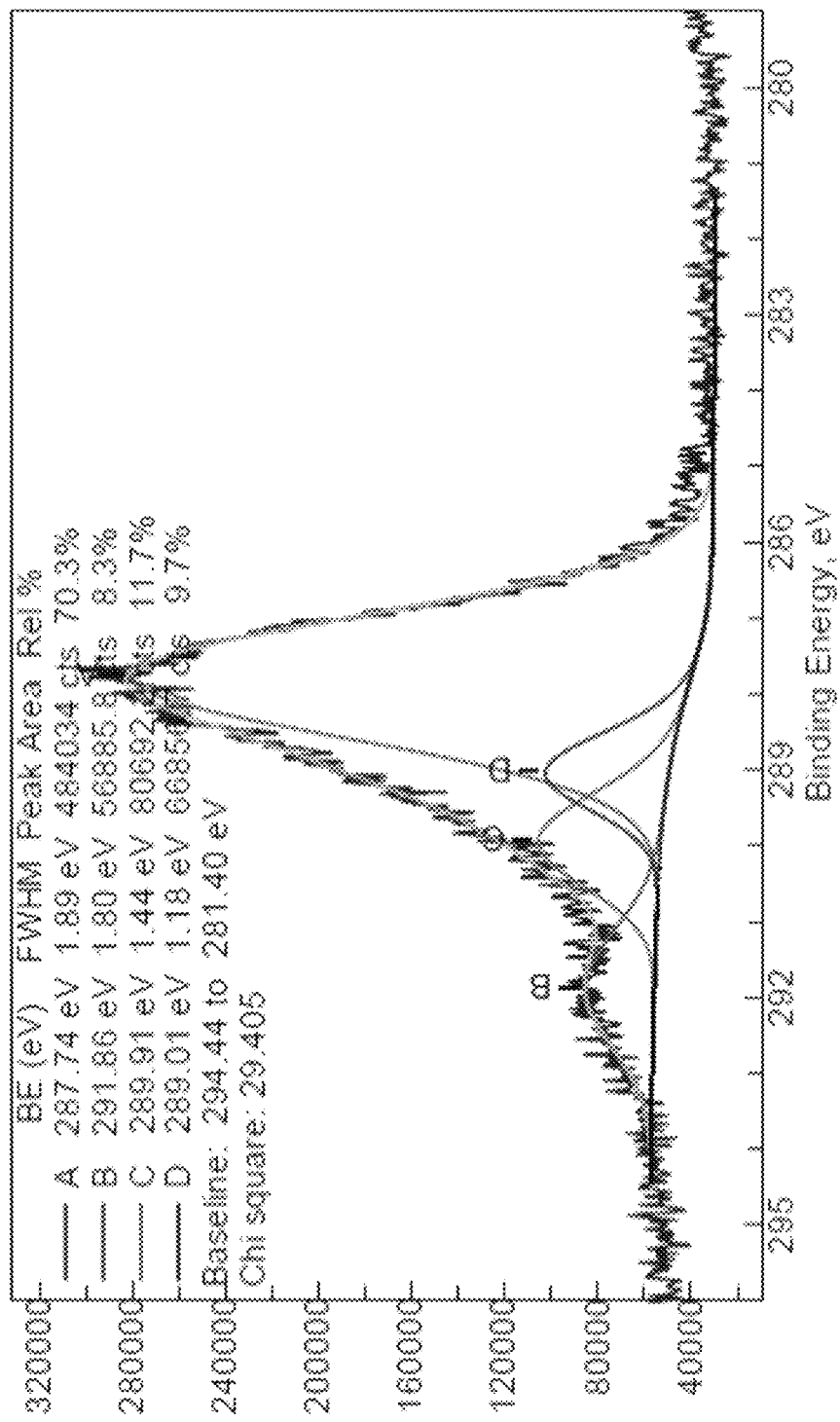
FIG. 4 shows a screenshot of an X-ray photoelectron spectrum analysis of humic acid.
Figure 5:
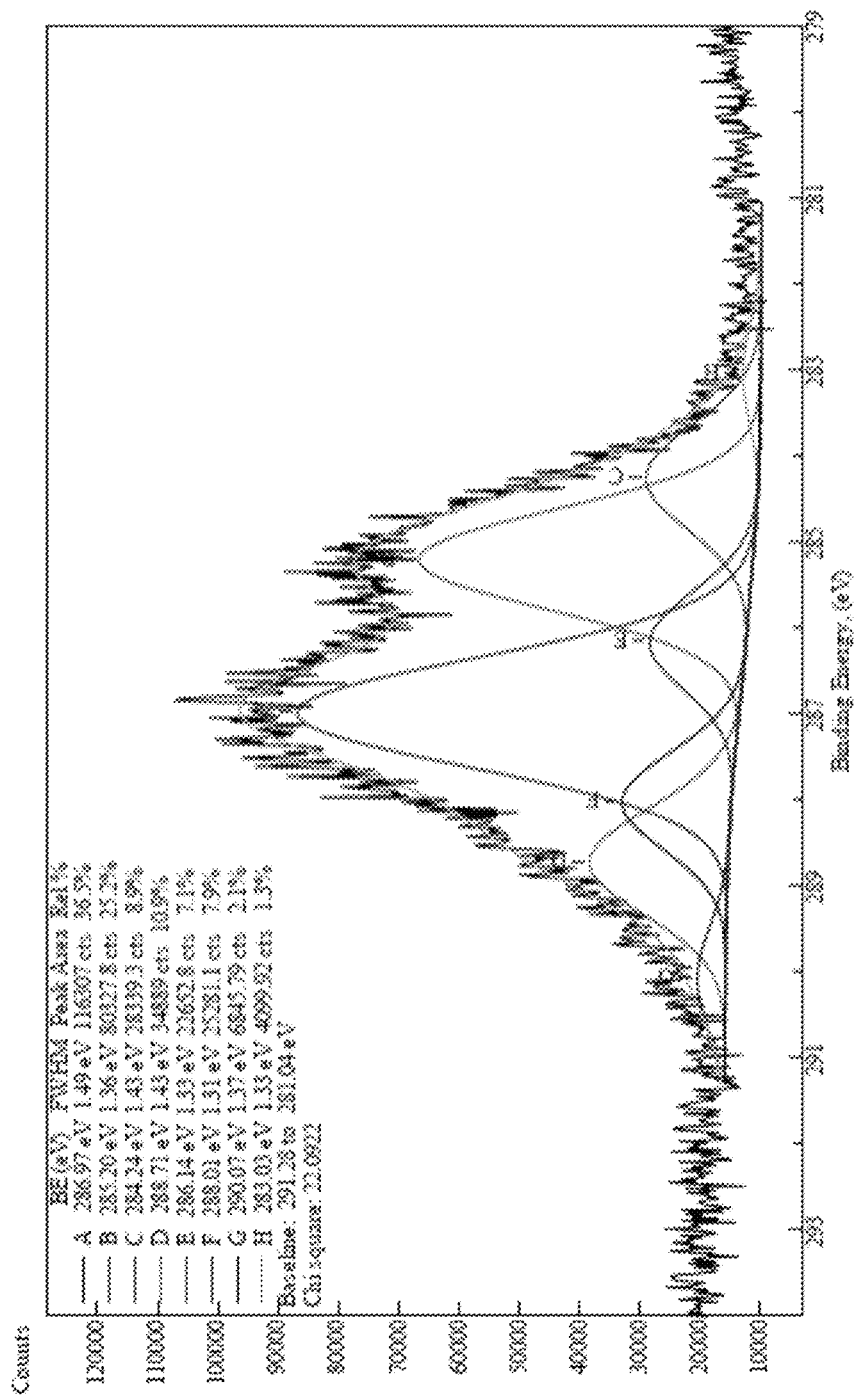
FIG. 5 shows a screenshot of an X-ray photoelectron spectrum analysis of humic acid after reduction with hydrazine.

FIGS. 4-6 compare the XPS of leonardite humic acid and that of graphenol. FIG. 4 shows the spectrum of humic acid; FIG. 5 shows the spectrum of humic acid reduced with hydrazine; and FIG. 6 shows the spectrum of humic acid reduced with hydrazine and then pyrolyzed at 370° C. (i.e. graphenol).

It can be seen in FIG. 6 that most of the carboxylic acid groups have been eliminated and the largest peak is C-OH peak. The IR spectrum (not shown) contains a large peak at around 3600 cm$^{-1}$, which is characteristic of OH.

The hydrogenation catalysts that have been tested so far include Raney nickel, copper chromium oxide, and ruthenium oxide. It appears that all of these catalysts work equally well, but any hydrogenation catalysts can be employed in the process.

An alternative method of producing graphene that has also been discovered involves:
First extracting leonardite, lignite, or peat with a strong base or dimethylformamide to create a dispersion of humic acid
Coating a substrate to form a thin film of the humic acid
Drying the film
Pyrolysis of the film under argon or argon/hydrogen at 400 to 800° C.

This process forms a thin layer of graphene on the substrate. In this process, one possible base is ammonium hydroxide dissolved in a water/alcohol mixture. The alcohol minimizes the "coffee stain" effect typically seen with just water solutions. Some alcohols known to be effective at this stage are methanol, ethanol and propanol. The ammonium hydroxide is advantageous as a base because in the drying step it can be evaporated away. Possible substrates are copper or nickel foils, but quartz, mica, or other suitable materials may also be used.

It has further been discovered that the graphenol or graphene particles can be dispersed and exfoliated into polymer systems and produce nanocomposites that exhibit improvements in physical properties never seen in clay or carbon nanotube polymer composites. The process of making these composites can be done in several different ways. The first method is to dissolve the polymer in a suitable solvent followed by dispersion of the graphenol or graphene with subsequent casting of films by removal of solvent. The second method is mainly applicable to the water dispersions of graphenol. In this method the graphenol dispersion is mixed with a polymer latex and then films are cast by letting the solvent evaporate. The third method involves the melt compounding of graphenol or graphene particles directly into the polymer melt in a high shear extruder. A fourth method is to incorporate the graphenol or graphene into the monomer system prior to polymerization and then to polymerize the polymer in the presence of the graphenol or graphene. Finally, the fifth method is to disperse the graphenol or graphene into one component of a thermoset resin such as an epoxy or urethane.

For the sake of concreteness, the following six examples are provided.

Example 1

Four Grams Of Agro-lig, a ground leonardite sample obtained from American Colloid Company, was dissolved in 400 mls. of 0.01 molar ammonium hydroxide. The solution was then filtered through a Gelman filter with pore size of 0.2 microns.

The solution was charged into a 2 liter Parr pressure reactor along with 3 grams of Cu 1950P that had previously been activated. The system was then purged three times with 200 psi of hydrogen. It was then pressurized to 320 psi of hydrogen and heated for 23 hours at 150° C. The catalyst was removed by filtration. The resulting colloidal suspension was stable even at low pH, indicating that all the acid functional groups had been reduced to alcoholic groups. Spin coated samples of this solution were imaged with SEM and AFM and demonstrated that carbonaceous sheets that are 1 to 2 atomic layers thick and with lateral dimensions in the micron range were produced.

Example 2

Two grams of Ago-lig were dissolved in 300 mls. of dimethylformamide and 32 mls. of water. Twenty mls. of hydrazine were added and the mixture placed in a round bottom flask equipped with a reflux column. The mixture was refluxed at 100° C. for 14 hours. The resulting colloidal suspension was stable even at low pH indicating that all the acid functional groups had been reduced to alcoholic groups. Spin coated samples of this solution were imaged with SEM and AFM and demonstrated that carbonaceous sheets that are 1 to 2 atomic layers thick and with lateral dimensions in the micron range were produced.

Example 3

Four grams of Agro-lig, a ground leonardite sample obtained from American Colloid Company, was dissolved in 400 mls. of 0.01 molar sodium hydroxide. The solution was then filtered through a Gelman filter with pore size of 0.2 microns. The solution was charged into a 2 liter Parr pressure reactor along with 3 grams of Raney nickel that had previously been activated. The system was then purged three times with 200 psi of hydrogen. It was then pressurized to 740 psi of hydrogen and heated for 23 hours at 150° C. The catalyst was removed by filtration. The resulting colloidal suspension was stable even at low pH, indicating that all the acid functional groups had been reduced to alcoholic groups. The solution was passed through a column of strong acid ion exchange resin to remove the sodium cations. Spin coated samples of this solution were imaged with SEM and AFM and demonstrated that carbonaceous sheets that are 1 to 2 atomic layers thick and with lateral dimensions in the micron range were produced.

Example 4

Four grams of Agro-lig, a ground leonardite sample obtained from American Colloid Company, was dissolved in 400 mls. of 0.01 molar alcoholic ammonium hydroxide. The base solution was made in a 1:1 ratio of water and ethyl alcohol. The solution was then filtered through a Gelman filter with pore size of 0.2 microns. This solution was then spin coated onto copper and nickel foils. The spin coated samples were then air dried. The samples were then heated in a tube furnace at 600° C. under an atmosphere of argon containing 5% by volume hydrogen.

The samples were then cooled and the resulting samples contained a film of graphene-like material covering the foil surface.

Example 5

The solution from example 1 was dried in air and ground to 325 mesh powder. The powder was then heated in a tube furnace under an atmosphere of argon containing 5% by volume of hydrogen for 5 hours at 700° C. The resulting powder was confirmed to be graphene by X-ray diffraction, XPS, and AFM.

Example 6

The solution from example 3 was mixed with a solution containing 1% polyvinyl alcohol. The solution was then cast to form a film containing 0.27% of the graphenol nanoparticles. The resulting composite yielded a modulus that was almost 5 times that of the pure polymer. The pure polymer had a tensile modulus of 164 mPa and the composite 780 mPa.

The foregoing description of the exemplary embodiments is provided to enable any person skilled in the art to make and use the disclosed subject matter. Various modifications to these embodiments will be readily apparent to those skilled in the art, and the generic principles defined herein may be applied to other embodiments without the use of the innovative faculty. Thus, the subject matter claimed is not intended to be limited to the embodiments shown herein but is to be accorded the widest scope consistent with the principles and novel features disclosed herein.

It is intended that all such additional systems, methods, features and advantages that are included within this description, be within the scope of the claims.

What is claimed is:

1. A process for making graphene, said process comprising the steps of:
providing a carbonaceous material;
extracting a humic acid solution from said carbonaceous material via a basic solution;
coating a substrate with said humic acid solution and drying said coated substrate to form a film;
pyrolytically reducing said film to graphene.

2. The process of claim 1, wherein said carbonaceous material comprises lignite or peat.

3. The process of claim 1, wherein said basic solution comprises ammonium hydroxide.

4. The process of claim 1, wherein said coating step comprises spin coating.

5. The process of claim 1, wherein said coating step employs a doctor blade or drawdown bar.

6. The process of claim 1, wherein said pyrolytic reduction is carried out under an inert atmosphere of noble gas.

7. The process of claim 1, wherein said pyrolytic reduction is carried out under an argon atmosphere, said argon atmosphere containing a partial pressure of hydrogen.

* * * * *